United States Patent [19]

Zondler et al.

[11] 4,352,913

[45] Oct. 5, 1982

[54] DIMETHYLAMINO DERIVATIVES AND THEIR USE

[75] Inventors: Helmut Zondler, Bottmingen; Roland Moser, Basel, both of Switzerland

[73] Assignee: Ciba-Geigy Corporation, Ardsley, N.Y.

[21] Appl. No.: 295,054

[22] Filed: Aug. 21, 1981

Related U.S. Application Data

[62] Division of Ser. No. 135,800, Mar. 31, 1980, Pat. No. 4,324,739.

[51] Int. Cl.$^3$ ................. C08G 59/42; C08G 59/50
[52] U.S. Cl. ........................ 525/504; 528/111; 528/121; 528/123; 528/361; 528/362; 528/365; 528/369; 528/370; 528/393; 528/407; 528/93
[58] Field of Search ............. 528/111, 121, 123, 365, 528/369, 370, 361, 362, 393, 407; 525/504

[56] References Cited

U.S. PATENT DOCUMENTS

| | | | |
|---|---|---|---|
| 2,326,721 | 8/1943 | Bruson | 260/465.5 |
| 2,642,412 | 6/1953 | Newey et al. | 528/121 |
| 2,753,323 | 7/1956 | Farnham | 528/123 |
| 2,965,672 | 12/1960 | Lott | 528/121 |
| 3,081,310 | 3/1963 | Rorig | 546/190 |
| 3,143,566 | 8/1964 | Surrey | 560/251 |
| 3,694,510 | 9/1972 | Moller et al. | 564/508 |
| 3,929,927 | 12/1975 | Marans et al. | 260/837 |
| 4,049,591 | 9/1977 | McEntire et al. | 521/129 |
| 4,088,614 | 5/1978 | Mori et al. | 521/163 |
| 4,110,358 | 8/1978 | Braunwarth | 260/404.5 |
| 4,201,854 | 5/1980 | Zondler et al. | 528/67 |

FOREIGN PATENT DOCUMENTS

961029 9/1954 Fed. Rep. of Germany .
362526 7/1962 Switzerland .

OTHER PUBLICATIONS

CA, 71, 40157d (1969).
CA, 52, 13807f (1958).
CA, 55, 10412e (1961).
CA, 50, 15582i (1956).
CA, 93, 98276n (1980).

*Primary Examiner*—Earl A. Nielsen
*Attorney, Agent, or Firm*—Luther A. R. Hall

[57] ABSTRACT

(Dimethylaminoalkyl)carboxylic and -carbamic acid esters and (dimethylaminoalkyl) ethers and ureas are compounds which are especially suitable for use as amine curing agents for polyepoxide compounds. They impart longer curing times to the curable mixtures and thus good processing properties, especially when the mixtures are used as adhesives. In addition, the mechanical properties are often improved. Further, these compounds afford advantages when used as curing agents on account of their low volatility.

3 Claims, No Drawings

DIMETHYLAMINO DERIVATIVES AND THEIR USE

This is a division of application Ser. No. 135,800 filed on Mar. 31, 1980 now U.S. Pat. No. 4,324,739, Apr. 13, 1982.

The present invention relates to (dimethylaminoalkyl) carboxylic and -carbamic acid esters and (dimethylaminoalkyl) ethers and ureas, and their use as amine curing agents in polyepoxide compounds containing on average more than one epoxy group in the molecule.

Epoxy resins are widely used in different technical fields, for example for surface protection, in the electrical and construction industries and as adhesives, laminating materials and moulding resins. In addition to containing various conventional additives, the epoxy resins contain curing agents, the composition of which must be matched e.g. to the processing conditions, the field of application and the product characteristics.

It is known to use N,N-dialkyl-1,3-propylenediamines as curing agents, either on their own (German Pat. No. 961,029) or together with "polyamide resins" (Swiss Pat. No. 362,526). Although these 1,3-propylenediamines have proved to be good curing agents, their use is not without disadvantages. On the one hand, they are relatively low-boiling substances which partially vapourise during processing for the production of epoxy resins and give rise to not entirely harmless odours. These odours can be eliminated only partially by the use of suction devices. On the other hand, a deposit of carbonate on processing machines resulting from the moisture and carbon dioxide content of the air is frequently observed.

N,N-Dialkyl-1,3-propylenediamines are still relatively reactive, so that the viscosity range in which the mixture can no longer be processed is reached within a short time of mixing the components. This viscosity is generally indicated by the gel time, which in this case is thus still regarded as being too short—a factor which results in technical disadvantages.

It has also already been proposed to use N,N-dimethyl-1,3-propylenediamine as curing agent in those polyepoxide compositions which are used as adhesives. Although very good adhesion is achieved by these means, there is a need to improve the adhesive action in order to be able to extend the field of use.

The object of the present invention is to provide curable mixtures of polyepoxide compounds which contain an amine curing agent, said mixtures having longer curing times and also an identical or improved adhesive action when used as adhesives. Preferably, the amine curing agents should be less volatile than e.g. N,N-dialkyl-1,3-propylenediamine.

Accordingly, the present invention provides dimethylamino derivatives of the formula I

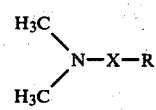   (I)

wherein
X is 1,3-propylene or ethylene or alkyl-substituted ethylene, and
R is the radical of the formulae

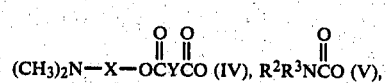

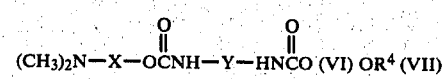

or OR$^{11}$OXN(CH$_3$)$_2$ (XI), wherein R$^1$ is alkyl, cycloalkyl, or aryl or aralkyl which is unsubstituted or substituted by halogen or C$_1$-C$_4$alkyl, Y is a direct bond, alkylene, alkenylene, cycloalkylene or arylene, R$^2$ is a hydrogen atom or has the meaning of R$^3$, and R$^3$ is alkyl, cycloalkyl, or aryl or aralkyl which is unsubstituted or substituted by C$_1$-C$_4$alkyl or halogen, R$^4$ is alkyl, alkenyl, cycloalkyl, cycloalkylalkylene, aryl or aralkyl which is unsubstituted or substituted by C$_1$-C$_4$alkyl or halogen, or is

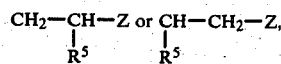

wherein R$^5$ is a hydrogen atom or methyl and Z is CN, CH$_2$NH$_2$ or CH$_2$N(CH$_3$)$_2$, and R$^{11}$ is alkylene, cycloalkylene or arylene, and X is additionally neopentylene if R is the radical OR$^4$, or
X is ethylene, 1,3-propylene or 1,3-propylene which is substituted in the 1- or 2-position by methyl, and R is the radical of the formulae

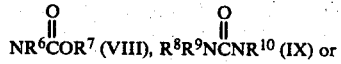

wherein each of X and Y independently is as defined above, n is 0 or 1, R$^6$ is a hydrogen atom, alkyl, cycloalkyl, β-cyanoethyl or β-cyanoethyl which is substituted in the 1- or 2-position by methyl, R$^7$ is alkyl, alkenyl, cycloalkyl, aryl, aralkyl, alkaryl or alkaralkyl, each of R$^8$ and R$^{10}$ is a hydrogen atom and R$^9$ is alkyl, cycloalkyl, aryl, aralkyl, alkaryl, alkaralkyl, 3-(dimethylamino)propyl, or each of R$^8$ and R$^9$ independently is C$_1$-C$_4$alkyl or phenyl and R$^{10}$ is a hydrogen atom or R$^8$ is a hydrogen atom, R$^9$ is alkyl, cycloalkyl, aryl, aralkyl, alkaryl or aralkaryl, and R$^{10}$ is β-cyanoethyl or β-cyanoethyl which is substituted in the 1- or 2-position by methyl.

Preferred derivatives are those wherein X in formula I is ethylene which is optionally substituted by C$_1$-C$_{12}$alkyl, preferably by C$_1$-C$_4$alkyl, and R is a radical of the formulae II to VII.

Further preferred derivatives are those wherein X in formula I is ethylene or 1,3-propylene and R is a radical of the formulae VIII to X.

R$^1$ in formula III is preferably C$_1$-C$_{12}$alkyl, especially C$_1$-C$_6$alkyl, C$_5$-C$_7$cycloalkyl, or phenyl or benzyl which is unsubstituted or substituted by C$_1$-C$_4$alkyl or halogen, preferably chlorine.

$R^2$ is formula V is preferably a hydrogen atom and $R^3$ is $C_1$-$C_{12}$alkyl, especially $C_1$-$C_4$alkyl, $C_5$-$C_7$cycloalkyl, phenyl or benzyl which is unsubstituted or substituted by $C_1$-$C_4$alkyl or halogen, preferably chlorine, or each of $R^2$ and $R^3$ independently is $C_1$-$C_4$alkyl, $C_5$-$C_7$-cycloalkyl or phenyl.

$R^4$ is formula VII is preferably alkyl or alkenyl of 1 to 18, preferably 1 to 12, carbon atoms, $C_5$-$C_8$cycloalkyl, $C_6$-$C_{16}$aryl, $C_7$-$C_{16}$aralkyl, β-cyanoethyl, γ-aminopropyl or γ-dimethylaminopropyl.

Y in formula IV is preferably a direct bond and in formulae IV and X is preferably alkylene or alkenylene of 1 to 12, preferably 1 to 6 carbon atoms, $C_5$-$C_7$cycloalkylene or $C_6$-$C_{12}$arylene.

$R^6$ as alkyl in formula VIII contains preferably 1 to 4 carbon atoms, and as cycloalkyl preferably contains 6 carbon atoms.

$R^7$ in formula VIII is preferably alkyl or alkenyl of 1 to 18, preferably 1 to 12, carbon atoms, $C_5$-$C_7$cycloalkyl, $C_6$-$C_{12}$aryl, $C_7$-$C_{16}$aralkyl or alkaryl or $C_8$-$C_{16}$alkaralkyl.

A preferred group of formula IX is one in which each of $R^8$ and $R^{10}$ is a hydrogen atom and $R^9$ is $C_1$-$C_{12}$alkyl, especially $C_1$-$C_6$alkyl, $C_5$-$C_7$cycloalkyl, $C_6$-$C_{12}$aryl, $C_7$-$C_{16}$aralkyl or alkaryl or $C_8$-$C_{16}$aralkaryl.

Another preferred group of the formula XI is that wherein each of $R^8$ and $R^9$ independently is $C_1$-$C_4$alkyl or phenyl, and $R^{10}$ is a hydrogen atom.

A further preferred group of the formula IX is that wherein $R^8$ is a hydrogen atom, $R^9$ is $C_1$-$C_{12}$alkyl, especially $C_1$-$C_6$alkyl, $C_5$-$C_7$cycloalkyl, $C_6$-$C_{12}$aryl, $C_7$-$C_{16}$alkaryl or aralkyl or $C_8$-$C_{16}$alkaralkyl, and $R^{10}$ is β-cyanoethyl or β-cyanoethyl which is substituted in the 1- or 2-position by methyl.

$R^{11}$ in formula XI is preferably $C_1$-$C_{12}$alkylene, $C_5$-$C_7$cycloalkylene or $C_6$-$C_{12}$arylene.

Examples of alkyl and alkenyl, which can be linear or branched, are: methyl, ethyl, propyl, isopropyl, n-butyl, isobutyl, tert-butyl, pentyl, hexyl, heptyl, octyl, nonyl, decyl, undecyl, dodecyl, tetradecyl, octadecyl, ethenyl, propenyl, isopropenyl, 1-butenyl, 2-butenyl, pentenyl, hexenyl, octenyl, dodecenyl, octadecenyl.

Examples of alkylene and alkenylene, which can be linear or branched, are: methylene, ethylene, 1,2- or 1,3-propylene, 1,2-, 1,3- or 1,4-butylene, pentylene, hexylene, 2-ethylbutylene, octylene, dodecylene, octylethylene, dodecylethylene, ethenylene, methylethenylene, dimethylethenylene, propenylene, butenylene, hexenylene, ethylethenylene, octylethenylene. Cycloalkylene can preferably be cyclopentylene, cycloheptylene, cyclooctylene and especially cyclohexylene. Arylene is preferably o-, m- and p-phenylene and naphthylene which can be substituted by $C_1$-$C_4$alkyl.

Cycloalkyl which can be substituted by $C_1$-$C_4$alkyl is e.g. cyclopentyl, cycloheptyl, cyclooctyl and especially cyclohexyl.

Aryl by itself or as moiety of aryl-containing groups is preferably naphthyl and especially phenyl. Examples of aralkyl, alkaryl or alkaralkyl are: benzyl, methylphenyl, methylnaphthyl, dimethylphenyl, diethylphenyl, ethylphenyl, butylphenyl, dibutylphenyl, octylphenyl, nonylphenyl, ethylmethylphenyl, benzyl, β-phenylethyl, γ-phenylpropyl, methylbenzyl, dimethylbenzyl, ethylbenzyl, butylbenzyl, dibutylbenzyl or nonylbenzyl.

The dimethylamino derivatives of the formula I are obtained by known methods in apparatus ordinarily used for the purpose.

The ethers of the present invention are obtained e.g. by etherifying alcohols of the formula $(CH_3)_2N$—X—OH with alcohols of the formula R—OH in the presence of a dehydrating agent, or reacting them with halides of the formula R—A, wherein A is halogen, preferably chlorine or bromine, optionally in the presence of a catalyst, or by addition of an alcohol of the formula $(CH_3)_2N$—X—OH to corresponding compounds having olefinic unsaturation.

The esters of the present invention are obtained by esterification or reaction of an alcohol of the formula $(CH_3)_2N$—X—OH with mono- or dicarboxylic acids or ester-forming derivatives thereof, e.g. anhydrides, esters or acid halides, optionally in the presence of a catalyst.

The carbamic acid esters of the present invention are obtained by the addition of alcohols of the formula $(CH_3)_2N$—X—OH to mono- or diisocyanates or by the reaction of about 1 mole of dicarboxylic acid ester with about 1 mole of amine of the formula

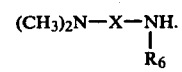

N-Substituents $R^2$, $R^3$ or $R^6$ can also be introduced by these reactions by reaction with corresponding halides or compounds having olefinic unsaturation.

The ureas of the present invention can be obtained by reaction of mono- or diisocyanates with amines of the formula

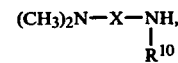

or by reaction of these amines with ureas which are unsubstituted or substituted by $R^8$ or $R^9$ substituents. The groups $R^8$, $R^9$ and $R^{10}$ can also be introduced by reaction with corresponding halides or compounds having olefinic unsaturation.

The starting alcohols and amines are commercially available or they can be readily obtained by addition of epoxides or acrylonitrile, methacrylonitrile or crotonitrile to dimethylamine, the resulting nitriles being subsequently hydrogenated to amines.

The dimethylamino derivatives of the formula I are most suitable for use as curing agents for epoxy resins. Accordingly, it is a further object of the invention to provide curable mixtures containing (a) a polyepoxide compound which contains on average more than one epoxy group in the molecule and (b) a curing agent which is a dimethylamino derivative of the formula I.

The dimethylamino derivatives of the formula I are usually added to the curable mixtures in amounts of 0.1 to 30 parts by weight, preferably 0.5 to 20 and in particular 1 to 15 parts by weight, based on the polyepoxide compound. They can be used on their own or together with other curing agents, in which case they frequently act as curing accelerators. Examples of known curing agents are acids such as di- and polycarboxylic acids, carboxylic acid anhydrides, polyhydric alcohols and phenols, polyamides, melamine/formaldehyde and urea/formaldehyde condensates, polyamines, polyisocyanates and phenoplast and aminoplast precondensates. Example of other suitable curing agents are polyaminoamides which are obtained from dimerised or trimerised fatty acids and aliphatic polyamines (cf.

Swiss Pat. No. 362,526). When used as curing accelerators or together with other curing agents, an amount of 0.1 to 5 parts by weight, based on the polyepoxide compounds, is usually sufficient.

The dimethylamines can also be used in the form of adducts, for example with liquid butadiene/nitrile copolymer which contains terminal carboxyl groups. If the curing agents contain active hydrogen atoms bonded to N atoms, the curable mixture preferably contains 1 equivalent of epoxide groups per 0.5 to 1.5 equivalents, especially about 1 equivalent, of these H atoms.

Polyepoxide compounds which can be used in the curable mixtures of the invention are, in particular, those which contain, on average, more than one glycidyl group, β-methylglycidyl group or 2,3-epoxycyclopentyl group bonded to a hetero-atom (for example sulfur and preferably oxygen or nitrogen); particularly preferred compounds are bis-(2,3-epoxycyclopentyl) ether; di- or polyglycidyl ethers of polyhydric aliphatic alcohols, such as 1,4-butanediol, or polyalkylene glycols, such as polypropylene glycols; di- or polyglycidyl ethers of cycloaliphatic polyols, such as 2,2-bis-(4-hydroxycyclohexyl)-propane; di- or polyglycidyl ethers of polyhydric phenols, such as resorcinol, bis-(p-hydroxyphenyl)-methane, 2,2-bis(p-hydroxyphenyl)-propane (=diomethane), 2,2-bis(4'-hydroxy-3',5'-dibromophenyl)-propane and 1,1,2,2-tetrakis-(p-hydroxyphenyl)-ethane, or of condensation products of phenols and formaldehyde which are obtained under acid conditions, such as phenol novolaks and cresol novolaks; di- or poly-(β-methylglycidyl) ethers of the above mentioned polyhydric alcohols or polyhydric phenols; polyglycidyl esters of polybasic carboxylic acids, such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidylaniline, N,N-diglycidyltoluidine and N,N,N',N'-tetraglycidyl-bis-(p-aminophenyl)-methane; triglycidyl isocyanurate; N,N'-diglycidylethyleneurea; N,N'-diglycidyl-5,5-dimethylhydantoin and N,N'-diglycidyl-5-isopropyl-hydantoin; and N,N'-diglycidyl-5,5-dimethyl-6-isopropyl-5,6-dihydro-uracil.

If desired, active diluents can be added to the polyepoxides in order to lower the viscosity. Examples of such diluents are styrene oxide, butyl glycidyl ether, isooctyl glycidyl ether, phenyl glycidyl ether, cresyl glycidyl ether or glycidyl esters of synthetic, highly branched and mainly tertiary aliphatic monocarboxylic acids ("CARDURA E").

Curing of the curable mixtures of the invention to produce mouldings and the like is advantageously carried out in the temperature range from 20° to 160° C. Curing can also be carried out in known manner as a two-stage or multistage process, in which case the first curing stage is carried out at a relatively low temperature and the after-curing is carried out at a higher temperature.

In many cases it may be desired to shorten the gel and curing times of the mixtures. For this purpose, it is possible to add known accelerators for amine curing, for example mono- or polyphenols, such as phenol or diomethane, salicyclic acid or salts of thiocyanic acid, such as NH$_4$SCN.

Furthermore, customary modifiers, such as extenders, fillers and reinforcing agents, pigments, dyes, organic solvents, plasticisers, flow control agents, thixotropic agents, flame retardants, mould release agents, can be added to the curable mixtures consisting of polyepoxide compounds and a dimethylamino derivative of the formula I, at any stage before final curing.

Examples of extenders, reinforcing agents, fillers and pigments which can be used in the curable mixtures of the invention are: coal tar, bitumen, liquid coumarone-/indene resins, textile fibres, glass fibres, asbestos fibres, boron fibres, carbon fibres, cellulose, polyethylene powders and polypropylene powders; quartz powder; mineral silicates, such as mica, asbestos powder or slate powder; kaolin, aluminium oxide trihydrate, chalk powder, gypsum, antimony trioxide, bentones, silica aerogel ("AEROSIL"), lithopones, barytes, titanium dioxide, carbon black, graphite, oxide colours, such as iron oxide, or metal powders, such as aluminium powder or iron powder.

Examples of organic solvents suitable for modifying the curable mixtures are toluene, xylene, n-propanol, butyl acetate, acetone, methyl ethyl ketone, diacetone alcohol, ethylene glycol monomethyl ether, ethylene glycol monoethyl ether and ethylene glycol monobutyl ether.

Examples of plasticisers which can be used to modify the curable mixtures are dibutyl phthalate, dioctyl phthalate and dinonyl phthalate, tricresyl phosphate, trixylenyl phosphate, diphenoxyethylformal andpolypropylene glycols.

Examples of flow control agents which can be added when the curable mixtures are used in particular in surface protection are silicones, liquid acrylic resins, cellulose acetobutyrate, polyvinylbutyral, waxes, stearates and the like (some of which are also used as mould release agents).

Particularly for use in the lacquer sector, the polyepoxide compounds can furthermore be partially esterified in known manner with carboxylic acids, such as, in particlar, higher unsaturated fatty acids. It is also possible to add other curable synthetic resins, for example phenoplasts or aminoplasts, to such surface-coating resin formulations.

The curable mixtures of the invention can be prepared in a conventional manner with the aid of known mixing equipment (stirrers, kneaders or rolls).

The curable epoxy resin mixtures are used, in particular, in the fields of surface protection, electrical engineering, laminating processes and adhesives technology and in the building trade. They can be used in a formulation suited in each case to the particular application, in the unfilled or filled state, if desired in the form of solutions or emulsions, as paints, lacquers, compression moulding compositions, injection moulding formulations, dipping resins, casting resins, impregnating resins and binders and as tooling resins, laminating resins, sealing and filling compositions, flooring compositions and binders for mineral aggregates.

The mixtures of the invention are preferably used as laminating resins and especially as adhesive resins.

The dimethylamino derivatives employed in the practice of this invention are liquid to viscous or crystalline substances which are of low volatility and which vapourise to only a slight extent even during processing of the mixtures of the invention, so that unpleasant odours scarcely arise during this processing. The curable mixtures the invention have surprisingly longer gel times (and thus improved processing possibilities) than those mixtures which contain N,N-dimethyl-1,3-propylenediamine, and give at least as good and in some cases better adhesive strength when used as adhesive resins.

The following Examples illustrate the invention in more detail.

PREPARATORY EXAMPLES

Example 1: β-Dimethylaminoethyl-β-cyanoethyl ether

(CH₃)₂NCH₂CH₂OCH₂CH₂CN 244 g of acrylonitrile are added dropwise to 356.5 g of 2-dimethylaminoethanol and 5 ml of Triton B in the course of 15 minutes. In the course of the ensuing exothermic reaction the mixture warms from room temperature to 75° C. While adding a further 5 ml of Triton B, the mixture is heated for 8 hours to 95° C. and then distilled. Yield: 451.4 g (79.4%) of analytically pure product (analysis by gas chromatography); b.p. 102° C./8 torr.

Example 2: γ-Dimethylaminopropyl-β-cyanoethyl ether

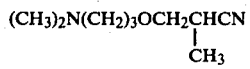
(CH₃)₂N(CH₂)₃OCH₂CHCN
                    |
                    CH₃

A mixture of 206.2 g of 3-dimethylamino-1-propanol and 161 g of methacrylonitrile is heated in the presence of 10 ml of Triton B for 10 to 68° C. in the manner described in Example 1. The catalyst is neutralised with 5 ml of glacial acetic acid and the mixture is taken up in 300 ml of chloroform and extracted with H₂O. The extract is concentrated and distilled, affording 148.8 g (44.3%) of more than 95% analytically pure product (analysis by gas chromatography) with a boiling point of 108° C./9 torr.

Example 3: β-Dimethylaminopropyl-(2)-β-cyanoethyl ether

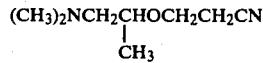
(CH₃)₂NCH₂CHOCH₂CH₂CN
            |
            CH₃

165 g of acrylonitrile are added dropwise to 268.0 g of 1-dimethylamino-2-propanol and 22 ml of 20% sodium hydroxide solution in the course of 1 hour at 55°–60° C. and the mixture is allowed to react for 1 hour at 55° C. A further 5 ml of 20% sodium hydroxide and 42 g of acrylonitrile are then added dropwise. After a further hour at 55° C. the reaction mixture is taken up in 100 ml of toluene and the solution is washed with a small amount of H₂O. Distillation yields 326.2 g (80.3%) of product with a boiling point of 103/10 torr.

EXAMPLE 4: β-Dimethylaminoethyl-γ-aminopropyl ether

(CH₃)₂NCH₂CH₂OCH₂CH₂CH₂NH₂

156.4 g of β-dimethylaminoethyl-β-cyanoethyl ether are hydrogenated in an autoclave in the presence of 550 ml of ethanol. 150 g of gaseous ammonia and 8 g of Raney nickel at 120° C. and a pressure of 135 atmos. Constant pressure is reached after 30 minutes. After removal of the catalyst, distillation of the solution yields 141.9 g (88.2%) of product with a boiling point of 78° C./10 torr.

Example 5: γ-Dimethylaminopropyl-γ-amino-isobutyl ether

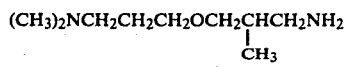
(CH₃)₂NCH₂CH₂CH₂OCH₂CHCH₂NH₂
                        |
                        CH₃

102 g of γ-dimethylaminopropyl-β-cyanoethyl ether are hydrogenated as in Example 4 in the presence of 350 ml of ethanol, 100 g of NH₃ and 8 g of Raney nickel at 120° C. and 120 atmos. Distillation yields 86.4 g (82.7%) of analytically pure product (analysis by gas chromatography) with a boiling point of 95° C./8 torr.

Example 6: β-Dimethylaminopropyl-(2)-γ-aminopropyl ether

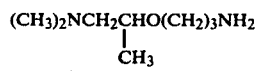
(CH₃)₂NCH₂CHO(CH₂)₃NH₂
            |
            CH₃

157.8 g of β-dimethylaminopropyl-(2)-β-cyanoethyl ether are hydrogenated as in Example 4 in the presence of 250 ml of isopropanol, 160 g of NH₃ and 15 g of Raney nickel at 105° C. and 110 atmos. Distillation yields 151.7 g (94.7%) of analytically pure product (analysis by gas chromatography) with a boiling point of 82° C./11 torr.

Example 7: β-Dimethylaminoethyl acetate

(CH₃)₂NCH₂CH₂OCOCH₃

With gentle cooling, 168.5 g of acetic anhydride are added dropwise to 133.6 g of 2-dimethylaminoethanol in the course of 20 minutes, whereupon the temperature rises from 20° C. to a maximum of 105° C. The reaction mixture is kept for 30 minutes at 100° C. and then cooled. Then 750 ml of CHCl₃ are added and the acetic acid formed is neutralised with 380 ml of 20% sodium hydroxide solution at 30°–35° C. with cooling. The two phases are separated and the organic phase is washed with a small amount of H₂O. Distillation of the residue affords 151.7 g (77.7%) of product with a boiling point of 114° C./225 torr.

Example 8: β-Dimethylaminopropyl acetate

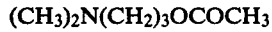
(CH₃)₂N(CH₂)₃OCOCH₃

14.4 g of 3-dimethylamino-1-propanol and 14.3 g of acetic anhydride are reacted and worked up as described in Example 7. Yield: 14.9 g (73.1%) of analytically pure product (analysis by gas chromatography) with a boiling point of 53° C./12 torr.

Example 9: γ-Dimethylaminopropyl propionate

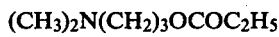
(CH₃)₂N(CH₂)₃OCOC₂H₅

10.8 g of 3-dimethylamino-1-propanol and 12.1 g of propionic anhydride are reacted and worked up as described in Example 7. Yield: 9.6 g (58.1%) of product with a boiling point of 85° C./20 torr.

Example 10: (2)-β-Dimethylaminopropyl isobutyrate

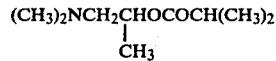
(CH₃)₂NCH₂CHOCOCH(CH₃)₂
            |
            CH₃

A solution of 107 g of isobutyryl chloride in 150 ml of CHCl₃ is added dropwise to 103 g of 1-dimethylamino-2

-propanol in 200 ml of chloroform. The reaction is exothermic and the mixture refluxes of its own accord. After a reaction time of 45 minutes, 210 ml of 20% NaOH are added dropwise at 25°–30° C. with cooling and the phases are separated. The organic phase is washed with 100 ml of water and concentrated. Distillation of the residue affords 127.7 g (74.0%) of product with a boiling point of 72° C./18 torr.

Example 11: γ-Dimethylaminopropyl laurate

(CH$_3$)$_2$N(CH$_2$)$_3$OCO(CH$_2$)$_{10}$CH$_3$

In accordance with the procedure of Example 10, 72.2 g of 3-dimethylamino-1-propanol and 153.1 g of lauryl chloride are reacted in altogether 250 ml of CHCl$_3$. The reaction mixture is neutralised with 147 ml of 20% NaOH. Yield: 157.2 g (82.1%) of product with a boiling point of 110° C./0.1 torr.

Example 12: β-Dimethylaminoethyl benzoate

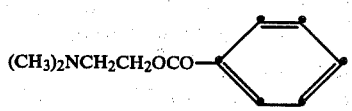

In accordance with the procedure of Example 10, 89.1 g of 2-dimethylaminoethanol and 140.5 g of benzoyl chloride are reacted in altogether 300 ml of CHCl$_3$. The reaction mixture is neutralised with 210 ml of 20% NaOH. Yield: 187.7 g (97.1%) of analytically pure product (analysis by gas chromatography) with a boiling point of 127° C./9 torr.

Example 13: β-Dimethylaminoethyl N-phenylcarbamate

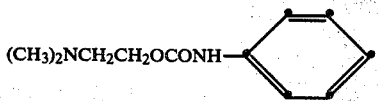

With cooling, 128 g of phenyl isocyanate are added dropwise to 96 g of dimethylaminoethanol at 60°–70° C. in the course of 45 minutes. After a further 30 minutes at 65° C., low boiling constituents are removed at a pressure of 0.02 torr and a bath temperature of 90° C. The residue (218.4 g=97.6%) is a light yellow fluid and consists substantialy of the above ester. Titration: 1 equivalent=208.4 g (theory 208.2). IR spectrum 3320 cm$^{-1}$ NH, 1720 cm$^{-1}$ C=O; no bands between 2000 and 2500 cm$^{-1}$, i.e. isocyanate is no longer present. Small amounts of 5–10 g can be distilled in a bulb tube at 135° C./0.015 torr; larger amounts decompose no distillation.

Example 14: γ-Dimethylaminopropyl N-cyclohexylcarbamate

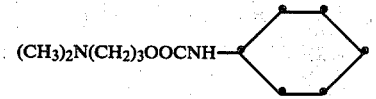

77.3 g of 3-dimethylamino-1-propanol are reacted with 94 g of cyclohexyl isocyanate in accordance with Example 13. Distillation of the reaction product yields 153.4 g (92.8%) of analytically pure product (analysis by gas chromatography) with a boiling point of 105° C./0.015 torr. IR spectrum: 3320 cm$^{-1}$ NH, 1700 cm$^{-1}$ C=O, no bands between 2000 and 2500 cm$^{-1}$.

Example 15: (2)-β-Dimethylaminopropy N-butylcarbamate

71.8 g of 1-dimethylamino-2-propanol are reacted with 69.0 g of butyl isocyanate in accordance with Example 13. Distillation yields 118.5 g (84.2%) of product with a boiling point of 72° C./0.015 torr. IR spectrum: 3340 cm$^{-1}$ NH, 1700 cm$^{-1}$ CO, no bands between 2000 and 2500 cm$^{-1}$.

Example 16: Toluylene 2,4-N,N'-bis-(β-dimethylaminoethyl carbamate)

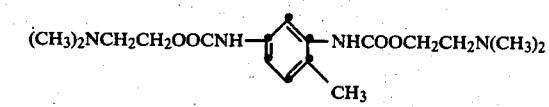

71.3 g of dimethylaminoethanol and 69.6 g of toluylene-2,4-diisocyanate are reacted in accordance with Example 13 at 70° C. to give 138.8 g of crude product. 125.1 g are recrystallised from 500 ml acetonitrile. Yield: 96.2 g (75.8%) with a melting point of 112°–113° C. EXAMPLE 17: β-Dimethylaminoethyl N-diethylcarbamate (CH$_3$)$_2$NCH$_2$CH$_2$OOCN(C$_2$H$_5$)$_2$ 500 ml of methylene chloride are added to 500 ml of a solution consisting of 99 g of phosgene and toluene and then a solution of 178 g of dimethylaminoethanol and 300 g of triethylamine in 500 ml of methylene chloride is added dropwise in the course of 1 hour at 10°–20° C. The reaction mixture is then refluxed for 2 hours, filtered and the filtrate is concentrated. Distillation of the residue in a high vacuum yields 136.5 g (72.5%) of product with a boiling point of 68°–72° C./0.01 torr. The NMR spectrum confirms the above structure.

EXAMPLE 18:
N-(n-butyl)-N'-(β-dimethylaminopropyl) urea (CH$_3$)$_2$NCH$_2$CH$_2$CH$_2$NHCONH(CH$_2$)$_3$CH$_3$ With stirring and cooling to 55°–60° C., 49.5 g of freshly distilled butyl isocyanate are added dropwise to freshly distilled 3-dimethylamino-1-propylamine under nitrogen in the course of 15 minutes. After 1 hour at 60° C., low boiling constituents are removed at a pressure of 0.1 torr and a maximum bath temperature of 140° C. Yield: 98.7 g (98%) of product of the above structure. Titration: 1 equivalent=208.3 g (theory 201.3 g).

Analysis C$_{10}$H$_{23}$N$_3$O (M=201.31): calculated: C 59.66 H 11.51 N 20.87 found: C 59.57 H 11.71 N 20.57

EXAMPLE 19: N-Phenyl-N'-(β-dimethylaminoethyl) urea $$(CH_3)_2NCH_2CH_2NH-CO-NH-\langle\text{phenyl}\rangle$$

88 g of dimethylaminoethylamine are dissolved in 500 l of toluene and then 119 g of phenyl isocyanate are added dropwise in the course of 10 minutes, whereupon the temperature rises to 97° C. The mixture is refluxed for 4 hours. On cooling, the product crystallises and is filtered with suction. The moist product is recrystallised from 1000 ml of ethyl acetate. Yield: 135 g (65.1%); m.p. 141°–142° C.

EXAMPLE 20: N-(n-Butyl)-N'-(β-cyanopropyl)-N'-(γ-dimethylamino-propyl)urea $$\begin{array}{c}(CH_3)_2N(CH_2)_3\\ \phantom{XXXX}\diagdown\\ \phantom{XXXXXXX}N-CONH(CH_2)_3CH_3\\ \phantom{XXXX}\diagup\\ NC-CHCH_2\\ \phantom{XX}|\\ \phantom{XX}CH_3\end{array}$$

Under nitrogen, a solution of 99.1 g of butyl isocyanate in 100 ml of methylene chloride is added dropwise in the course of 1 hour to a solution of 169.3 g of N-(β-cyanopropyl)-dimethylaminopropylamine in 500 ml of methylene chloride. The mixture is then refluxed for 2 hours, concentrated, and the residue is treated at 80° C. in a high vacuum in order to remove all low boiling constituents. Yield: 249.2 g (90.8%) of product in the form of an oil. Titration: 1 equivalent=261.9 g (theory 268.4 g).

Analysis $C_{14}H_{28}N_4O$ (M=268.41): calculated: C 62.65 H 10.52 N 20.88. found: C 62.5 H 10.5 N 20.6

EXAMPLE 21: N,N'-Dimethylaminopropyl urea $$(CH_3)_2N(CH_2)_3NH-CO-NH(CH_2)_3N(CH_3)_2$$

A mixture of 204 g of dimethylaminopropylamine and 60 g of urea is gradually heated to 140° C. in the course of 2 hours and kept at this temperature overnight. NH$_3$ gas evolves from the resultant clear solution. The mixture is heated for a further 5 hours to 200° C. and then cooled. Distillation yields 126.1 g (54.8%) of urea of the above structure with a boiling point of 183°–185° C./0.1 torr.

Analysis $C_{11}H_{26}N_4O$ (M=230.36): calculated: C 57.36 H 11.38 N 24.32. found: C 57.2 H 11.3 N 24.2

EXAMPLE 22: Hexamethylene-N,N-bis-(γ-dimethylaminopropyl) urea $$(CH_3)_2N(CH_2)_3NHCONH(CH_2)_6NH-CONH(CH_2)_3N(CH_3)_2$$

204.3 g of dimethylaminopropylamine are added dropwise to a solution of 168.2 g of hexamethylene diisocyanate in 100 ml of methylene chloride and the mixture is refluxed overnight, in the process of which crystals precipitate. The crystals are filtered with suction at room temperature, washed with CH$_2$Cl$_2$ and dried. Recrystallisation from a mixture of 1000 ml of acetone and 800 ml of ethanol yields 221.0 g (59.3%) of product with a melting point of 159° C. Tritration: 2 equivalents=376.7 g (theory 372.6 g).

EXAMPLE 23: β-Dimethylaminoethylcarbamate $$[(CH_3)_2NCH_2CH_2O]_2CO$$

Using a 80 cm packed column with controlled head, ethanol is slowly distilled off from a mixture consisting of 118 g of diethyl carbonate, 178 g of 2-dimethylaminoethanol and 0.66 g of KOH. Distillation of the resultant crude product (153 g) yields 82.4 g of a mixture with a boiling point of 88°–120° C. at 14 torr. Distillation of 77 g of this mixture over a spinning band column yields 41.7 g of product with a boiling point of 111° C./14 torr. Titration: 1 equivalent=101.6 g (theory 102.1 g). The NMR spectrum confirms the above structure.

EXAMPLE 24: β-Dimethylaminoethyl-γ-dimethylaminopropyl ether $$(CH_3)_2NCH_2CH_2OCH_2CH_2CH_2N(CH_3)_2$$

With cooling, 250 g of formic acid are added dropwise to 158 g of β-dimethylaminoethyl-γ-aminopropyl ether (prepared in accordance with Example 4). Then 187 ml of a 38% aqueous formaldehyde solution are added dropwise at 55°–65° C. in the course of 1 hour, with evolution of CO$_2$. The temperature is then gradually raised to 116° C., stirring is continued for a further 17 hours, then 224 g of conc. HCl are added, and the reaction mixture is concentrated by rotary evaporation. After addition of a solution of 125 g of NaOH in 400 ml of H$_2$O the amine precipitates in the form of an oil. The oil is separated and the aqueous phase is extracted with four 50 ml portions of toluene. Distillation of the extracts and the amine yields 101.4 g (54.2%) of pure amine with a boiling point of 110° C./13 millibar. The first runnings contain further amounts of amine. The IR spectrum of the pure amine shows no NH bands above 3000 cm$^{-1}$.

EXAMPLE 25: β-Dimethylaminopropyl-(2)-γ-dimethylaminopropyl ether $$\begin{array}{c}(CH_3)_2NCH_2CHOCH_2CH_2CH_2N(CH_3)_2\\ \phantom{XXXXXX}|\\ \phantom{XXXXXX}CH_3\end{array}$$

The following batch is reacted and worked up as in Example 24: 49.7 g of β-dimethylaminopropyl-(2)-γ-aminopropyl ether, 71 g of formic acid, 54 ml of 38% formaldehyde, 64 g of conc. HCl and a solution of 75 g of NaOH in 300 ml of H$_2$O. The amine is extracted with toluene and distillation of the extracts affords 41.4 g of analytically pure amine (analysis by gas chromatography) with a boiling point of 110°/20 millibar.

EXAMPLE 26: Benzyl-γ-dimethylaminopropyl ether $$\langle\text{phenyl}\rangle-CH_2OCH_2CH_2CH_2N(CH_3)_2$$

The following batch is reacted and worked up as in Example 24: 77 g of benzyl-γ-aminopropyl ether, 107 g of formic acid, 80 ml of 38% formaldehyde, 48 g of conc. HCl, and a solution of 35 ml of NaOH in 350 ml of H$_2$O. After extraction of the amine, distillation of the extracts yields 55.6 g (61.8%) of pure amine with a boiling point of 134° C./20 millibar. The IR spectrum shows no NH bands above 3000 cm⁻¹.

EXAMPLE 27: Cyclohexyl-γ-dimethylaminopropyl ether

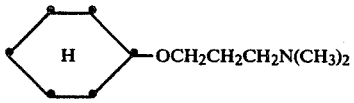

The following batch is reacted and worked up as in Example 24: 180 g of cyclohexyl-γ-aminopropyl ether, 250 g of formic acid, 190 ml of 38% of formaldehyde, 113 g of conc. HCl, and a solution of 66 g of NaOH in 200 ml of H₂O. Distillation yields 121.5 g (60.2%) of analytically pure amine (analysis by gas chromatography) with a melting point of 115°/18 millibar.

EXAMPLE 28: Dodecyl-γ-dimethylaminopropyl ether

CH₃(CH₂)₁₁OCH₂CH₂CH₂N(CH₃)₂

The following batch is reacted and worked up as in Example 24: 191 g of dodecyl-γ-aminopropyl ether, 180 g of formic acid, 38% formaldehyde, 81 g of conc. HCl, and a solution of 98 g of NaOH in 500 ml of H₂O. The amine is extracted with a mixture of butanol/hexane. Distillation yields 99.6 g (48.4%) of analytically pure amine (analysis by gas chromatography) with a boiling point of 130° C./0.06 millibar.

EXAMPLE 29: Undecyl-(2)-γ-dimethylaminopropyl ether

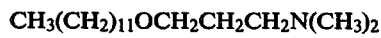

The following batch is reacted and worked up as in Example 24: 70.3 g of undecyl-γ-aminopropyl ether, 70 g of formic acid, 53 ml of 38% formaldehyde, 32 g of conc. HCl, and a solution of 23 g of NaOH in 350 ml of H₂O. The amine is extracted with three 100 ml portions of butanol. Distillation yields 37.8 g (47.9%) of amine with a boiling point of 110° C./0.06 millibar.

EXAMPLE 30: 1,4-Cyclohexyl-di-(γ-dimethylaminopropyl) ether

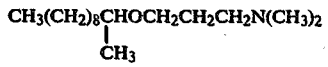

The following batch is reacted and worked up as in Example 24: 66.1 g of 1,4-cyclohexyl-di-(γ-aminopropyl) ether which contains a small amount of 4-hydroxycyclohexyl-γ-aminopropyl ether owing to incomplete cyanoethylation and hydrogenation, 132 g of formic acid, 100 ml of 38% formaldehyde, 60 g of conc. HCl, and a solution of 38 g of NaOH in 250 ml of H₂O. Concentration of the reaction mixture yields 77 g of crude amine. Distillation over a packed column yields an analytically pure diamine (analysis by gas chromatography) with a boiling point of 89° C./0.005 millibar.

EXAMPLE 31: Di-(γ-dimethylaminopropyl) terephthalate

A solution of 61 g of terephthalyl chloride in 200 ml of CHCl₃ is added dropwise at 45°–50° C. to a solution of 81.9 g of 3-dimethylamino-1-propanol in 450 ml of chloroform, whereupon crystals precipitate. After a further reaction time of 15 minutes, 132 g of a 20% NaOH solution are added dropwise at 25° C., whereupon the crystals dissolve. The organic phase is separated and concentrated. Distillation of the residue yields 65.4 g of pure amine (65.5%) with a boiling point of 157° C./0.04 millibar.

EXAMPLE 32: Di-(β-dimethylaminoethyl) adipate (CH₃)₂NCH₂CH₂OOC-(CH₂)₄COOCH₂CH₂N(CH₃)₂

A solution of 91.5 g of adipyl dichloride in 400 ml of CHCl₃ is added dropwise to 89 g of dimethyl aminoethanol in 400 ml of CHCl₃ at 45°–50° C. Then 220 ml of a 20% NaOH solution is added dropwise at 25° C. and the organic phase is separated. The aqueous phase is extracted with three 100 ml portions of CHCl₃. Concentration of the extracts yields 141 g of crude product. Distillation yields 76.3 g (53%) of pure product with a boiling point of 160° C./0.03 millibar.

EXAMPLE 33: Di-(β-dimethylaminopropyl) dodecanediate

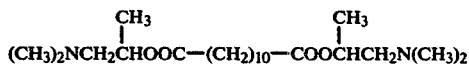

A solution of dodecanediyl chloride in 350 ml of CHCl₃ is added dropwise at 45°–50° C. to 51.6 g of 3-dimethylamino-2-propanol in 250 ml of CHCl₃. Then 110 ml of 20% NaOH are added dropwise at 25° C. The organic phase is separated and the aqueous phase is extracted with two 100 ml portions of CHCl₃. All the organic phases are concentrated (97.4 g). Distillation of 92 g affords 50.6 g (53.5%) of analytically pure amine (analysis by gas chromatography) with a boiling point of 163°/0.03 millibar.

(B) USE EXAMPLE

The dimethylamino derivatives listed in Table I are mixed with a liquid epoxy resin based on bisphenol A and epichlorohydrin (epoxide content 5.4 val/kg; viscosity according to DIN 53 015 at 25° C.: 10,500 mPaS). The content of dimethylamino derivatives is indicated in parts by weight per 100 parts by weight of epoxy resin.

The adhesive strength is determined by measuring the shear strength of ground degreased Anticorrodal 100-B samples with 12 mm overlap (shear tension test according to DIN 53 282). Curing time: 3 hours at 100° C.

The gel time is determined at 120° C. using sample amounts of ½ g on a thermostatically controlled heating plate.

TABLE I

| Dimethylamino derivative | Amount | Gel time min. | Gel time sec. | Shear strength ($N/mm^2$) |
|---|---|---|---|---|
| $D(CH_2)_2O(CH_2)_3NH_2$ | 14.3 | 2 | 40 | 12.9 |
| $D(CH_2)_2O(CH_2)_2CN$ | 16 | 2 | 55 | 21.0 |
| $D(CH_2)_3OCH_2CH(CH_3)CN$ | 19.2 | 4 | 30 | 15.8 |
| $D(CH_2)_3OCH_2CH(CH_3)CH_2NH_2$ | 17.0 | 2 | 45 | 18.7 |
| $D(H_2CC(CH_3)_2CH_2O(CH_2)_2CN$ | 15.5 | >210 min. | | 12.4 |
| $DCH_2CH(CH_3)O(CH_2)_2CN$ | 17.6 | 10 | 0 | 16.1 |
| $DCH_2CH(CH_3)O(CH_2)_3NH_2$ | 15.7 | 4 | 40 | 18.3 |
| $D(CH_2)_3-O-CH_2-\langle O \rangle$ | 21.6 | 8 | 50 | 19.2 |
| $D(CH_2)_3-O-\langle H \rangle$ | 20.8 | 7 | 25 | 18.5 |
| $D(CH_2)_3-O-CH(CH_2)_8CH_3$ / $CH_3$ | 29.3 | 33 | 15 | 14.2 |
| $DCH_2-CH-O-(CH_2)_3-D$ / $CH_3$ | 10.6 | 6 | 35 | 14.3 |
| $D(CH_2)_2-O-(CH_2)_3-D$ | 9.8 | 5 | 55 | 16.3 |
| $D(CH_2)_3-O-\langle H \rangle-O-(CH_2)_3-D$ | 16.1 | 7 | — | 14.4 |
| $D(CH_2)_2OCOCH_3$ | 14.8 | 15 | 50 | 17.9 |
| $D(CH_2)_3OCOCH_3$ | 14.2 | 8 | 50 | 20.9 |
| $D(CH_2)_3OCOCH_3$ | 10.7 | 10 | 40 | 19.0 |
| $D(CH_2)_3OCOC_2H_5$ | 15.6 | 10 | 10 | 21.2 |
| $D(CH_2)_3OCOC_2H_5$ | 11.7 | 8 | 50 | 18.8 |
| $D(CH_2)_3OCOn-C_{11}H_{23}$ | 32.2 | 19 | 0 | 23.0 |
| $DCH_2CH(CH_3)OCOCH(CH_3)_2$ | 19.5 | 46 | 0 | 19.9 |
| $D(CH_2)_2OCOC_6H_5$ | 16.4 | 15 | 0 | 23.2 |
| $D(CH_2)_3OCC-\langle O \rangle-COO(CH_2)_3D$ | 19.0 | 6 | 25 | 18.8 |
| $DCH_2-CHOCC-(CH_2)_{10}-COO-CHCH_2-D$ / $CH_3$ / $CH_3$ | 22.5 | 18 | 05 | 19.8 |
| $D(CH_2)_2OOC(CH_2)_4-COO(CH_2)_2D$ | 16.3 | 10 | 30 | 22.0 |
| $D(CH_2)_2NHCONHC_6H_5$ | 23.4 | 2 | 55 | 15.5 |
| $D(CH_2)_3N\langle CONH-n-C_4H_9 / CH_2CH(CH_3)CN \rangle$ | 30.2 | 12 | 0 | 16.2 |
| $[D(CH_2)_3NH]_2CO$ | 13.0 | 2 | 15 | 12.6 |
| $[D(CH_2)_3NHCONH]_2(CH_2)_6$ | 15.8 | 2 | 40 | 14.5 |
| $D(CH_2)_2OCON(C_2H_5)_2$ | 13.8 | 25 | 20 | 18.0 |
| $D(CH_2)_2OCONHC_6H_5$ | 17.6 | 8 | 50 | 19.5 |
| $D(CH_2)_3OCONHC_6H_{11}$ | 25.7 | 7 | 30 | 19.0 |
| $DCH_2CH(CH_3)OCONHC_4H_9$ | 22.8 | 19 | 0 | 23.1 |
| 2,4-Toluylen[$NHCOO(CH_2)_3D]_2$ | 14.9 | 7 | 20 | 14.7 |
| $[D(CH_2)_2O]_2CO$ | 11.5 | 8 | 20 | 16.7 |
| | 12.5 | 1 | 35 | 16.4 |
| $D(CH_2)_3NH_2$ | 10 | 1 | 50 | 15.0 |
| (comparison) | 5 | 3 | 25 | 12.6 |

D in the table denotes the $(CH_3)_2N-$ group.

USE EXAMPLE II

The dimethylamino derivatives listed in Table II are mixed with a liquid epoxy-phenol-novolak resin (epoxide content 5.68 val/kg). The content of dimethylamino derivative is indicated in parts by weight per 100 parts by weight of epoxy resin. The test conditions for determining the adhesive strength and the gel time are the same as those indicated in Use Example I.

TABLE II

| Dimethylamino derivative | Amount | Gel time min. | Gel time sec. | Shear strength (N/mm²) |
|---|---|---|---|---|
| D—(CH₂)₃—NH₂ (comparison) | 10.5 | — | 55 | 10.7 |
| D—(CH₂)₃—O—CH₂—⌬ | 22.7 | 3 | 20 | 12.1 |
| D—(CH₂)₃—O—CH(CH₃)—CH₂—D | 11.1 | 2 | 45 | 9.0 |
| D—(CH₂)₃—O—CO—C₆H₄—CO—O—(CH₂)₃—D | 20.0 | 3 | 20 | 15.8 |
| [D—CH₂—CH(CH₃)—O—CO]₂(CH₂)₁₀— | 23.7 | 11 | 25 | 13.3 |

USE EXAMPLE III

The dimethylamino derivatives listed in Table III are mixed with a liquid diglycidyl tetrahydrophthalate of technical quality (epoxide content 6.1 val/kg; viscosity 600 mPas/25° C.). The content of dimethylamino derivative is indicated in parts by weight per 100 parts by weight of epoxy resin.

The test conditions for determining the adhesive strength and the gel time are as indicated in Use Example I.

USE EXAMPLE IV

The dimethylamino derivatives listed in Table IV are mixed with a liquid hydantoin glycidyl ether of technical quality (epoxide content 7.2 val/kg; viscosity 1250 mPas/25° C.).

The content of dimethylamino derivative is indicated in parts by weight per 100 parts by weight of epoxy resin.

The test conditions for determining the adhesive strength and the gel time are as indicated in Use Example I.

TABLE III

| Dimethylamino derivatives | Amount | Gel time min. | Gel time sec. | Shear strength (N/mm²) |
|---|---|---|---|---|
| D—(CH₂)₃—NH₂ (comparison) | 11.3 | 3 | — | 13.2 |
| D—(CH₂)₃—HN—CO—NH(CH₂)₃—D | 14.7 | 4 | — | 15.0 |
| D—(CH₂)₃—O—CH(CH₃)—CH₂—D | 12.0 | 3 | 50 | 10.8 |
| [D—CH₂—CH(CH₃)—O—CO]₂(CH₂)₁₀— | 25.4 | 17 | 20 | 12.4 |

TABLE IV

| Dimethylamino derivative | Amount | Gel time min. | Gel time sec. | Shear strength (N/mm²) |
|---|---|---|---|---|
| D—(CH₂)₃—NH₂ (comparison) | 13.3 | 1 | 9 | 11.3 |
| D—(CH₂)₂—O—(CH₂)₂CN | 21.3 | 2 | 25 | 10.3 |
| D—(CH₂)₃—O—CH₂—⌬ | 28.8 | 9 | 20 | 8.9 |
| D—(CH₂)₃—O—CH(CH₃)—CH₂—D | 14.1 | 4 | 45 | 9.9 |
| D—(CH₂)₂—O—CO—CH₃ | 19.7 | 22 | — | 12.2 |

TABLE IV-continued

| Dimethylamino derivative | Amount | Gel time min. | Gel time sec. | Shear strength (N/mm²) |
|---|---|---|---|---|
| D—(CH$_2$)$_3$—O—C(=O)—N(H)—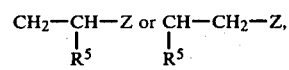 | 34.3 | 10 | — | 12.2 |
| D—(CH$_2$)$_3$—O—C(=O)—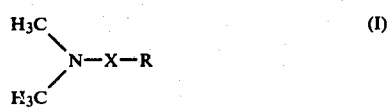—C(=O)—O—(CH$_2$)$_3$—D | 25.3 | 7 | 45 | 14.8 |
| [D—CH$_2$—CH(CH$_3$)—O—C(=O)]$_2$(CH$_2$)$_{10}$— | 30.0 | 36 | 40 | 14.9 |

What is claimed is:

1. A curable mixture containing (a) a polyepoxide compound which contains on average more than one epoxy group in the molecule and (b) a curing agent which is a dimethylamino derivative of the formula I $$\begin{array}{c} H_3C \\ \phantom{H_3C}\diagdown \\ \phantom{H_3CC}N-X-R \\ \phantom{H_3C}\diagup \\ H_3C \end{array} \quad (I)$$

wherein
X is 1,3-propylene or ethylene or alkyl-substituted ethylene, and
R is the radical of the formulae (CH$_3$)$_2$N—X—OCO (II), R$^1$CO (III), (CH$_3$)$_2$N—X—OCYCO (IV), R$^2$R$^3$NCO (V), (CH$_3$)$_2$N—X—OCNH—Y—HNCO (VI), OR$^4$ (VII) or OR$^{11}$OXN(CH$_3$)$_2$(XI), wherein R$^1$ is alkyl, cycloalkyl, or aryl or aralkyl which is unsubstituted or substituted by halogen or C$_1$–C$_4$ alkyl, Y is a direct bond, alkylene, alkenylene, cycloalkylene or arylene, R$^2$ is a hydrogen atom or has the meaning of R$^3$, and R$^3$ is alkyl, cycloalkyl, or aryl or aralkyl which is unsubstituted or substituted by C$_1$–C$_4$alkyl or halogen, R$^4$ is alkyl, alkenyl, cycloalkyl, cycloalkylalkylene, or aryl or aralkyl which is unsubstituted or substituted by C$_1$–C$_4$ alkyl or halogen, or is $$\begin{array}{cc} CH_2-CH-Z & \text{or} \quad CH-CH_2-Z, \\ \phantom{CH_2-}| & \phantom{or CH-}| \\ \phantom{CH_2-}R^5 & \phantom{or CH-}R^5 \end{array}$$

wherein R$^5$ is a hydrogen atom or methyl and Z is CN, CH$_2$NH$_2$ or CH$_2$N(CH$_3$)$_2$, and R$^{11}$ is alkylene, cycloalkylene or arylene, and X is additionally neopentylene if R is the radical OR$^4$, or X is ethylene, 1,3-propylene or 1,3-propylene which is substituted in the 1- or 2-position by methyl, and
R is the radical of the formulae NR$^6$COR$^7$ (VIII), R$^8$R$^9$NCNR$^{10}$ (IX) or (CH$_3$)$_2$N—X—NHC(=O)—NH—(Y—NHC(=O)NH)$_n$ (X), wherein each or X and Y independently is as defined above, n is 0 or 1, R$^6$ is a hydrogen atom, alkyl, cycloalkyl, β-cyanoethyl or β-cyanoethyl which is substituted in the 1- or -2 position by methyl, R$^7$ is alkyl, alkenyl, cyclalkyl, aryl, aralkyl, alkaryl or alkaralkyl, each of R$^8$ and R$^{10}$ is a hydrogen atom and R$^9$ is alkyl, cycloalkyl, aryl, aralkyl, alkaryl, alkaralkyl, 3-(dimethylamino) propyl, or each of R$^8$ and R$^9$ independently is C$_1$–C$_4$ alkyl or phenyl and R$^{10}$ is a hydrogen atom or R$^8$ is a hydrogen atom, R$^9$ is alkyl, cycloalkyl, aryl, aralkyl, alkaryl or aralkaryl, and R$^{10}$ is β-cyanoethyl or β-cyanoethyl which is substituted in the 1- or 2-position by methyl.

2. A process for the production of a cured mixture consisting of a polyepoxide compound containing on average more than one epoxy group in the molecule and a curing agent, which process comprises heating the polyepoxide compound in the presence of a dimethylamino derivative of the formula I according to claim 1.

3. A process according to claim 2, wherein the mixture is heated at the most to below the decomposition temperature of the polyepoxide compound, preferably to a temperature not exceeding 150° C.

* * * * *